United States Patent [19]

Castino

[11] 4,420,398

[45] Dec. 13, 1983

[54] FILTERATION METHOD FOR CELL PRODUCED ANTIVIRAL SUBSTANCES

[75] Inventor: Franco Castino, Sudbury, Mass.

[73] Assignee: American National Red Cross, Washington, D.C.

[21] Appl. No.: 292,582

[22] Filed: Aug. 13, 1981

[51] Int. Cl.³ .................. B01D 13/00; B01D 31/00
[52] U.S. Cl. ................................. 210/641; 210/645; 210/648; 210/651; 210/181; 210/182; 210/195.2; 210/257.2; 210/259; 210/295; 210/321.1; 210/335; 435/68; 435/240; 435/241; 435/803; 435/811; 424/85
[58] Field of Search ............. 210/641, 645, 648, 650, 210/651, 774, 779, 790, 805, 806, 181, 182, 195.2, 257.2, 259, 295, 321, 335, 433.2, 927; 435/68, 240, 241, 803, 811; 424/85

[56] References Cited

U.S. PATENT DOCUMENTS

| | | | |
|---|---|---|---|
| 3,256,152 | 6/1966 | Lampson | 435/68 |
| 3,506,126 | 4/1970 | Serfass et al. | 210/96.2 |
| 3,579,441 | 5/1971 | Brown | 204/180 |
| 3,926,797 | 12/1975 | Gigou et al. | 210/638 |
| 3,939,069 | 2/1976 | Granger et al. | 210/637 |
| 4,013,564 | 3/1977 | Nose | 210/434 |
| 4,191,182 | 3/1980 | Popovich et al. | 128/214 R |
| 4,209,392 | 6/1980 | Wallace | 210/646 |
| 4,212,742 | 7/1980 | Solomon et al. | 210/247 |
| 4,216,770 | 8/1980 | Cullis et al. | 128/214 R |
| 4,223,672 | 9/1980 | Terman et al. | 128/214 R |
| 4,243,532 | 1/1981 | Tsuda et al. | 210/196 |

OTHER PUBLICATIONS

Kauppinen, H. L. et al. "Large Scale Production and Properties of Human Leukocyte Interferon . . . ", In, *Human Interferon Production and Clinical Use*, W. R. Stinebrins, Ed., Plenum Press, N.Y. 1977 pp. 1–13.

Porter, M. C. et al., "Membrane Ultrafiltration", in *Chemical Tech.* Jan. 1971 pp. 56–63.

Yabrov, A. A., *Interferon and Nonspecific Resistance*, Human Science Press, N. Y., 1980 pp. 28–31, 135, 136, 175–184.

Michaels, A. S. "New Separation Technique For The CPI", *Chem. Eng. Progress*, vol. 64, No. 12, 1968 pp. 31–43.

*Primary Examiner*—David R. Sadowski
*Attorney, Agent, or Firm*—Holman & Stern

[57] ABSTRACT

This invention affords a filtration method and apparatus for extracting cell produced antiviral substances (CPAS) from a production broth using cross-flow membrane filtration. The broth is perfused into a first filtration cell and caused to cross-flow across an ultrafiltration membrane in the cell, permitting a first filtrate to pass through the membrane consisting essentially of CPAS and some molecular species and retaining in a first ex-filtrate all remaining portions of the broth.

24 Claims, 3 Drawing Figures

FILTERATION METHOD FOR CELL PRODUCED ANTIVIRAL SUBSTANCES

BACKGROUND OF THE INVENTION

1. Field of the Invention

This invention relates to a filtration method for extracting cell produced antiviral substances (CPAS) from a production broth using cross-flow membrane filtration.

2. Description of the Prior Art

"Cell Produced Antiviral Substances" (CPAS) are defined for purposes of this invention as proteins that inhibit virus multiplication which are produced by (a) infecting animal (including human) cells with animal viruses, (b) exposure of animal cells to mitogens, certain synthetic polynucleotides, etc., or (c) by hybridomas and genetically engineered bacterial cell lines. As used in this invention, CPAS includes interferons of all types, lymphokines, monoclonal antibodies produced by hybridomas, and the products of genetically engineered cell lines. All of these substances are distinguished for the purposes of this invention from viral chemotherapy agents, vaccines, defective interfering particles, viral interference substances, and the like.

Where the CPAS is not produced by hybridomas or genetically engineered cell lines, it must be induced in natural cell lines by a "CPAS Inducer", which is defined for purposes of this invention as any substance which will cause a cell to produce CPAS, including viruses, mitogens, synthetic polynucleotide/RNA sources, tilorone hydrochloride, lymphomycin, purified protein derivative of tuberculin, OK-432, and the like. Animal viruses range in size from 10 to 300 nm and have molecular weights upwards of $1 \times 10^6$ daltons. They therefore are easily filtered by the cross-flow cells useful in this invention.

CPAS is produced by the cells themselves in a "Production Broth" which is defined for the purposes of this invention as a mixture of producing cells which may be a suspension of hybridomas or genetically engineered CPAS producing bacterial cell lines or a suspension of naturally-occurring animal cells with a CPAS inducer, and which may also contain cellular particles, various molecular species of differing molecular weights and configurations, diluents, salts, and various incubation media.

One of the continuing problems in the production of various CPAS is the extraction of a relatively pure CPAS from the production broth. Conventional extraction techniques either cannot efficiently separate the CPAS from other substances in the production broth, cannot separate the CPAS from some contaminents, or destroy the producing bacteria, hybridomas, or cells of the production broth, making a continuous or semi-continuous flow process impossible.

Cross-flow filtration is a relatively new separation technique. Cross-flow filtration cells or similar filtration cells are disclosed in U.S. Pat. Nos. 4,191,182 - Popovich, et al., and 4,212,742 - Solomon, et al., which, however, do not disclose their use in the manner of the present invention.

Additional patents of interest which are not considered to disclose the present invention, include the following:

U.S. Pat. No. 3,926,797 discloses a blood purifying apparatus having a conventional filtration cell and a conventional dialysis cell.

U.S. Pat. No. 4,216,770 - Cullis, et al., discloses a continuous flow treatment for carbamylating red blood cells wherein (1) the red blood cells and plasma are separated, (2) the red blood cells are mixed with an anti-sickle cell agent, (3) the treated cells are separated from waste material, (4) the treated cells are washed, (5) the washed cells are separated from waste material, and (6) recombined with the plasma and returned to the patient. The separations are apparently by gravity without using filtration cells or dialysis cells.

U.S. Pat. No. 4,223,672 - Terman, et al., discloses a system and apparatus for removal of immunological reactants from blood wherein (1) plasma is separated from whole blood by a cell separator (filter) [see column 2, lines 46-55] or by a centrifuge, (2) the plasma is treated with an immunoabsorbent in a variable volume plasma treatment chamber, (3) platelets are removed from the plasma in a platelet separation "bag" 55 [see column 2, lines 31-34 and column 5, lines 20-24], and (4) the separated platelets and other blood components are recombined. The immunoabsorbent is fixed to a carrier vehicle [column 5, lines 53-58] and centrifugation is described extensively [column 6, line 28 et seq.].

U.S. Pat. No. 3,579,441 - Brown discloses blood purification by dual filtration. FIGS. 1A and 2 disclose using both an ultrafilter 40 with blood flow parallel to the filter elements 43 and a hyperfilter 60. The ultrafiltrate under pressure is fed to the hyperfilter, also parallel to the filtering surfaces. The Abstract of the Disclosure has a brief description of the flow pressure.

U.S. Pat. No. 4,209,392 - Wallace discloses a hemodialysis circuit with a single plasma separator (membrane filter) and a sorbents filter in the closed loop.

U.S. Pat. No. 4,243,532 - Tsuda, et al., discloses separating plasma from whole blood using a Kiil-type filtration cell, and an in-line adsorbent filtration apparatus [FIG. 5] for purifying the plasma, after which it is recombined with the other blood components. Centrifugal separation is disclosed as undesirable [column 5, lines 21-28].

U.S. Pat. No. 3,506,126 - Serfass, et al., discloses a closed recirculating hemodialysis system using a single ultrafilter cell for its water/dialysate filtration and selective adsorbers for waste metabolites.

U.S. Pat. No. 3,939,069 - Granger, et al., discloses a conventional dialysis circuit with one dialysis membrane and an in-line charcoal adsorbing filter.

U.S. Pat. No. 4,013,564 - Nose discloses a conventional dialysis circuit [FIG. 9] and apparatus.

HUMAN LEUKOCYTE INTERFERON PRODUCTION - A TYPICAL CPAS

Although the present invention is not limited to any particular CPAS, it is useful for background purposes to discuss the production of human leukocyte interferon (HuIFN-α) which is a typical CPAS. The comments regarding HuIFN-α production would be applicable mutatis mutandis to many other CPAS, particularly interferons and most particularly human interferons.

"Interferons" are defined for purposes of this invention as cell-specific small proteins that inhibit virus multiplication (by protecting cells from viral cytolysis). They may be produced by genetically engineered bacteria manufactured by recombinant DNA technology; as well as by cells infected with a stimulant (inducer)

which may be animal viruses, (either live or killed), and which contain either DNA or RNA (including double-stranded RNA and single-stranded RNA with stable base-paired loops), among others. Interferons being cell-specific, different types of interferons are produced by different types of cells in which interferon production is induced by various substances. Known types of human interferons include alpha-type from human leukocyte cells with a virus inducer (HuIFN-α) having a molecular weight range of about 15,000 to 21,000 daltons, beta-type from human fibroblast cells with a virus inducer (HuIFNβ) having a molecular weight of about 24,000 daltons, gamma-type from human leukocyte cells with a mitogen inducer (HuIFNγ) having a molecular weight range of about 40,000 to 70,000 daltons, and lymphoblastoid cell interferon. It is quite possible that other human interferons exist, than those above identified.

A "Mitogen", for the purposes of this invention, may be defined as a substance that induces mitosis and, in particular, induces the production of interferons in animal cells. Examples of mitogens known to induce interferons are pokeweed mitogen, lipopolysaccharid, Epstein-Barr virus, phytohemagglutinin, lymphocytosis-promoting factor, and pertussis B mitogen.

Interferons also may be induced by various synthetic RNA (polyneucleotide) sources, including Poly (I:C), Poly (I:C:L:C), Poly (I:C:L), Poly (A:2I), Poly (A:U) and the like.

Hybridomas are cloned hybrid cells which produce monoclonal antibodies. They are made by fusing an antibody-producing cell with a tumor cell. Although not all monoclonal antibodies have antiviral properties, they are all included within the term CPAS for the purposes of this invention.

HuIFN-α is currently produced for clinical purposes by the technique introduced by Cantell [Cantell, et al., "Human Leukocyte Interferon: Production, Purification, Stability, and Animal Experiments" in *The Production And Use Of Interferon For The Treatment And Prevention Of Human Virus Infections*, Waymouth, (ed), the Tissue Culture Association, Rockville, Maryland, 1974, page 37, with some subsequent modifications [Cantell, et al., "Preparation of Human Leukocyte Interferon for Clinical Use", Texas Rep. Biol. Med. 35:138, 1977].

Leukocytes for HuIFN-α production according to this invention, may be obtained by any means, for example, from buffy coats, plateletpheresis residues, etc.

The technique utilized by Cantell, 1974 and Cantell, 1977 for the extraction of HuIFN-α from leukocyte suspensions is essentially fractional precipitation, preceded by virus inactivation at acid pH, and followed by ethanol extraction and further purification. On the order of 50% of the HuIFN-α activity may be lost in this process, and the final product shows the presence of contaminants, typically serum albumin.

Fractional precipitation processes are based on the different solubility of various components of a mixture.

HuIFN or other CPAS could also be separated from the production broth by centrifugation techniques; however, such techniques act to destroy the producing cells, and, therefore, are only useful for batch production, as distinguished from a continuous-flow or semi-continuous-flow production method.

There are many other CPAS sources from which CPAS can be purified and extracted according to this invention. The invention is therefore not limited to any particular CPAS or production broth. Examples of various CPAS include, but are not limited to, the following.

Immune interferon was produced by human lymphocyte cultures after treatment with the CPAS Inducer ionophore A 23187.

Immune interferon appeared in the culture fluid (production broth) when spleen cells derived from C57BL/6 mice immunized with L cells 7 days previously were cocultured with antigenic cells.

Interferon has been produced by mouse fibroblast cells using various DNA and RNA viruses as CPAS inducers, including F and H strains of Newcastle disease virus, Sendai virus, GD-7, Mengo, and vesicular stomatis virus, and herpes simplex 1. It should be noted that cross-species interferon responses have been reported between humans and other primates and between humans and rodents. This invention therefore encompasses interferons produced from cells of all animal species.

Interferon has been produced by human fibroblast cells using Poly (I:C) as a CPAS inducer, together with a variety of interferon-associated proteins of 15,000–70,000 daltons.

Interferon has also been produced by human lymphoblastoid cells.

The nucleic acid sequences of several interferons produced by human fibroblasts and leukocytes have been isolated and cloned by recombinant DNA techniques. *Escherichia coli* bacteria were "engineered" to synthesize pure interferon.

Lymphokines, defined broadly as lymph node activating factors, have been synthesized by lymphoid cells of different origins and are believed to be important for immunogenesis, for regulation of the immune response, and for inhibition of microphage migration. Lymphokines of various types have been induced in murine leukocytes by lectins (Con A, *Wistaria floribunda* mitogen, and nonmitogenic hemagglutinin from *W. floribunda* seeds).

Cloned T-cell hybridomas have been induced with concanavilin-A to release factors (monoclonal antibodies) stimulating the B-cell response to antigen.

Known additional CPAS purification includes the disclosure in "The Complete Purification of Human Leucocyte Interferon", Berg, K. and Heron, I., Scand. J. Immunol., 11 (5), 489–502 (1980) whose abstract states: "Human leucocyte interferon (HuLeIF) has for the first time been purified by a series of techniques involving precipitation, gel filtration, and affinity chromatography with Cu-chelate, blue dextran, and antibody. The 2 major species of HuLeIF were identified as clearly separable and stainable proteins representing 85% of the biological activity with mol wt 18,400 and 20,180 daltons. Three more subspecies of HuLeIF were demonstrated with mol wt 19,500, 20,900 and 22,130 daltons, representing 15% of the biological activity. Specific activity of pure interferon is $2 \times 10^9$ interferon units/mg protein. Recovery was about 50%, and the purification factor exceeded 350,000." [HuLeIF is the old nomenclature for HuIFN.]

SUMMARY OF THE INVENTION

The present invention provides a method for extracting cell-produced antiviral substances (CPAS) from a production broth comprising subjecting the broth to a cross-flow membrane filtration wherein the broth is perfused into a first filtration cell and caused to cross-flow across an ultrafiltration membrane in said cell, permitting a first filtrate to pass through said membrane, which first filtrate consists essentially of CPAS and some molecular species, and retaining in a first ex-filtrate remaining portions of said broth.

In another embodiment, a diafiltration process may be afforded by a partially-closed cycle continuous flow, in which the filtrate removed from the broth is replaced with an equal volume of media, thus maintaining a constant suspension volume throughout the process, and the ex-filtrate is cycled back to the broth.

In still another embodiment, a dual module filtration process may be afforded by perfusing the first filtrate containing the CPAS into a second filtration cell and causing it to cross-flow across a second filtration membrane in said cell, which second membrane permits a second filtrate to pass through it, which second filtrate consists essentially of molecules smaller than the CPAS, which second filtrate is then discarded, the CPAS molecules being retained in the second ex-filtrate.

In yet another embodiment, a dual module diafiltration process is afforded by perfusing the first filtrate containing the CPAS into a second filtration cell and causing it to cross-flow across a second filtration membrane in said cell, which second membrane permits a second filtrate to pass through it, which second filtrate consists essentially of molecules smaller than the CPAS, which second filtrate is then recycled to the broth with the first ex-filtrate, maintaining an approximately constant suspension volume in a partially-closed cycle continuous flow process, the purified CPAS being in the second ex-filtrate.

In a further embodiment, from 1 to 3 or more additional filtration cells may be incorporated within the cycle, whereby the CPAS of the second ex-filtrate is further purified by the filtration removal of molecular species and other impurities, which molecular species and other impurities either are recycled to the production broth or are discarded, all recovered CPAS being pooled.

It is an important advantage of this invention that it reduces or substantially eliminates damage to the CPAS-producing cells, thus permitting a continuous- or semi-continuous-flow production process. To achieve this, it is important that the maximum wall shear rate of the conduit, pumps, cross-flow filtration cell, and any other part of the circuit through which these cells travel not exceed the point at which the cells are lysed or otherwise damaged. In the case of leukocytes, for example, the preferred maximum wall shear rate in the flow circuit is about 1,500 $s^{-1}$.

DESCRIPTION OF THE PREFERRED EMBODIMENTS

In the present invention, cross-flow filtration techniques are applied to the separation of a CPAS from its production broth, and for further purification by removal of extraneous material and contaminants.

The cross-flow filtration techniques used in this invention may be considered as "high pass/low pass" (or the reverse), in that a first filtration separates the CPAS and smaller particles from larger particles, and a second filtration separates the CPAS from the smaller particles. The order of filtration may be reversed, when desired. However, where the producing cells are to be returned to the production broth intact, it is preferable that the ex-filtrate in the first filtration contain all particles larger than the CPAS, so that the CPAS and all smaller particles are contained in the first filtrate.

Filtration other than cross-flow, is outside the scope of this invention, at least for the filtration step in which the CPAS and producing cells are separated, because conventional, or "dead-end" filtration tends to lyse the producing cells and because the cells and other large particles tend to accumulate at the cell membrane, reducing or completely blocking separation of the CPAS.

The cross-flow filtration can be carried out in either one of two modes: (a) filtration only; or (b) diafiltration (where the filtrate is replaced with an equal volume of media, diluent or recycled waste, maintaining a constant suspension volume throughout the process). These processes have been successfully utilized for membrane plasmapheresis, hemofiltration, virus filtration, and separation of proteins, and have proven less traumatic to labile components than other separation processes.

Previous work in the separation of proteins by ultrafiltration has indicated that the nature of the membrane, the fluid mechanics of the system, and the composition of the suspension are the most important determinants of separation efficiency. Membranes with cut-off properties permitting the separation of, for example, human leukocyte interferon size molecules from larger molecules are available. Furthermore, generalized conditions for this separation can be extrapolated from other systems which have already been examined. These include human serum albumin (HSA)+lysozyme and HSA+alpha-lactalbumin in water.

By choosing proper membrane filter parameters, up to 100% of CPAS has been recovered. Factors that effect the choice include both particle size and particle configuration. The object is to separate as close to the CPAS as possible, with maximum separation efficiency (minimum CPAs non-removal), and minimum nondesirable particles.

For the above reasons, the first filtration cell membrane should have a nominal molecular weight cut-off of at least about twice, and preferably up to about five times, the maximum molecular weight of the CPAS. This takes into account variations in molecular configuration. For example, if the CPAS is an HuIFN-α molecule with a molecular weight range of about 15,000 to 21,000 daltons, the first membrane should be sized to pass all molecules and particles having a molecular weight smaller than at least 40,000 daltons, and preferably up to 100,000 daltons.

In some instances, the CPAS may be associated with another molecule (for example, HuIFN-α with HSA), in which case the nominal molecular weight cutoff of the membrane must take into consideration the combination.

The second filtration cell membrane, which separates the CPAS from smaller molecules and particles, should be chosen so that the nominal nolecular weight cut-off is less than about 75 percent (preferably, about 75 percent) of the minimum molecular weight of the CPAS. For example, if the CPAS is an HuINF-α interferon molecule with a molecular weight range of 15,000 to 21,000 daltons, the second membrane should be sized to pass all molecules smaller than about 11,250 daltons. The second filtration cell is preferably, but does not have to be, a cross-flow filtration cell.

The exact sizing of the membranes must take into consideration that the molecular weight of a particular CPAS is approximate and will vary over several thousand daltons, that the molecular configuration is variable, and that membranes are not available in an infinite range of sizes.

While CPAS producing cells or genetically engineered bacteria are grossly larger than the CPAS itself, and therefore easily separated, certain other substances present in the production broth may be of similar size to the CPAS, or even smaller. For example, where the CPAS is an HuIFN-γ interferon molecule, which has a weight range of about 40,000 to 70,000 daltons, and where the CPAS inducer has a molecular weight of 30,000 daltons, the CPAS inducer will pass with the CPAS through the first filtration membrane. In such an instance, the CPAS inducer can be separated from the CPAS in the second filtration cell and either discarded or recycled to the production broth. Regardless of the CPAS inducer, it is usually preferable to recycle the CPAS-producing cells or bacteria back to the production broth.

So that the CPAS inducer may be cleanly separated from the CPAS, it is advisable that it be chosen so that it is either (a) two times (preferably ten times) larger than the CPAS molecule range to be produced, or (b) 0.5 times (preferably 0.1 times) smaller than the CPAS molecule range to be produced. If the CPAS inducer is larger than the CPAS, it is retained in the first ex-filtrate, if smaller, it passes with the second filtrate.

Figure 1:
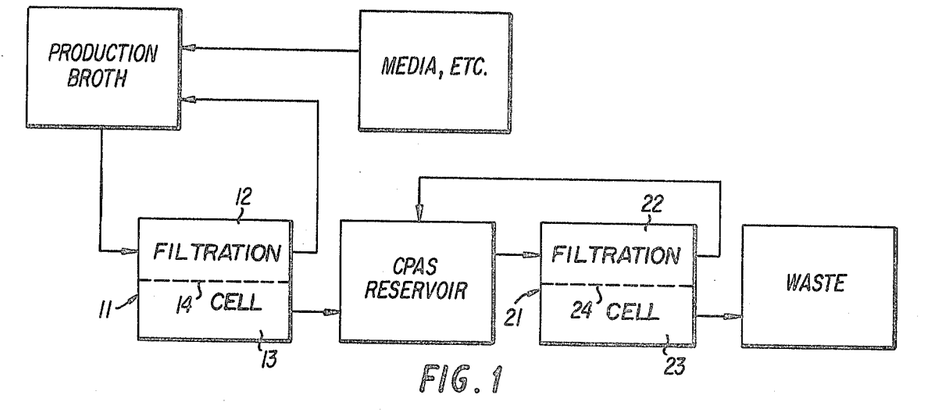
FIG. 1 is a flow chart of the apparatus and method of this invention wherein the second filtrate is discarded and additional media and adjuvants are added to the production broth.

FIG. 1 is a flow diagram of one embodiment of this invention, in which the production broth flows to a first cross-flow filtration cell 11, entering ex-filtrate chamber 12. As the CPAS production broth flows across membrane 14, the CPAS, some low molecular weight species, and other contaminants of lower molecular weight or smaller configuration than the CPAS pass through the membrane 14 and enter filtrate chamber 13. The ex-filtrate is then recycled from chamber 12 back to the production broth. The filtrate containing the CPAS then flows to a CPAS Reservoir. The CPAS in the CPAS Reservoir is further purified by removal of waste matter such as the low molecular weight species. This may be accomplished by a second cross-flow filtration cell 21 connected to the CPAS Reservoir in a recirculation mode, so that the CPAS, small molecular particles and other contaminants, flow from the CPAS Reservoir, enter ex-filtrate chamber 22 and cross-flow across membrane 24. Membrane 24 is chosen so that the molecular species and other contaminants smaller than the CPAS pass through it and enter chamber 23 while the CPAS molecules are retained in chamber 22 and are recycled to the CPAS Reservoir. The filtrate from chamber 23 may be discarded as waste matter, in which instance media is added to the production broth in a quantity approximately equal to that of the waste matter discarded. Liquid flow is maintained by conventional pumping means, a constant flow rate pump being preferred. It is also preferred that the filtrate flow rates throughout the entire system be maintained as equal.

Figure 2:
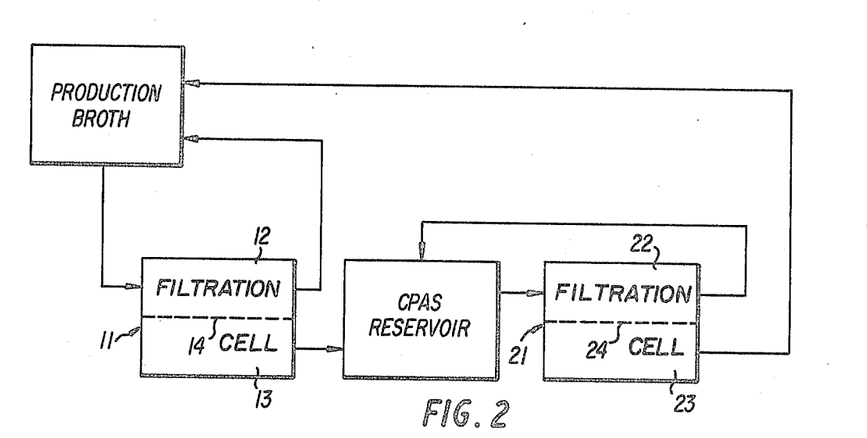
FIG. 2 is a flow chart of the apparatus and method of this invention wherein the second filtrate is recycled to the production broth.

FIG. 2 is a flow diagram for a second embodiment of this invention. In FIG. 2 the production broth flows to a first cross-flow filtration cell 11 which may be the same as or different from that shown in FIG. 1. The production broth enters ex-filtrate chamber 12 and cross-flows across filtration membrane 14, whose size is chosen to permit the CPAS molecules and all molecular species smaller than the same to flow through it into chamber 13, forming the first filtrate. The ex-filtrate from chamber 12 is recycled to the production broth. The first filtrate from filtration cell 11 flows to the CPAS Reservoir where it is further purified by passing through a second filtration cell 21 in a recirculation mode. The CPAS and smaller molecular species from the CPAS Reservoir flow to the ex-filtrate chamber 22. Filtration membrane 24 is selected in a size such that molecules smaller than the CPAS may pass through it. The CPAS becomes the second ex-filtrate and is recycled from chamber 22 back to the CPAS Reservoir. The molecular species smaller than CPAS entering chamber 23 become the second filtrate and are recycled back to the production broth. Because this is a closed cycle, no media need be added to the production broth until the CPAS has become sufficiently purified and is removed from the CPAS Reservoir. To maintain a constant flow rate, producing cells, media, and CPAS inducer (if necessary) may be added to the production broth in a total volume approximately equal to the waste removed from the CPAS Reservoir.

As a variation of FIG. 1 (which is not shown), the CPAS Reservoir/second filtration cell flow circuit may be converted to a diafiltration circuit by introducing a diluent, such as water, flowing either into the CPAS reservoir or into the second filtration cell, which will act to remove salts and molecular species smaller than the CPAS. In such an instance, the total waste will be equal to the volume of the first filtrate plus the added diluent.

Figure 3:
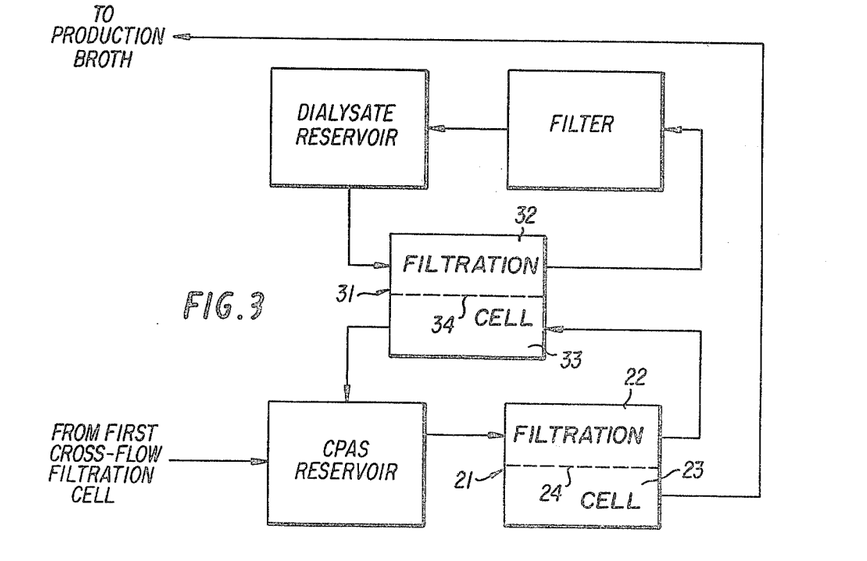
FIG. 3 is a flow chart of an embodiment of this invention wherein a dialysis circuit is included in a conduit between the CPAS reservoir and the second filtration cell.

In a third embodiment shown in FIG. 3, an auxillary diafiltration circuit may be added at some point between the exit of the second ex-filtrate from the first cross-flow filtration cell (not shown) and its entry into the CPAS Reservoir (not shown). Any conventional diafiltration cell may be used, and would be particularly useful for removing contaminant salts and other dissociating molecules which are in the second ex-filtrate. In FIG. 3, the relatively purified CPAS from chamber 32 (the second ex-filtrate) flows to a standard dialysis cell 31 and enters chamber 33, flowing past membrane 34 and exiting to be returned to the CPAS Reservoir. A suitable dialysate fluid is circulated by conventional pumping means from a Dialysate Reservoir to chamber 32 of the dialysis cell 31, preferably in a direction opposite to the flow of the CPAS, and upon leaving chamber 32, having attracted the contaminating molecules to be removed from the CPAS through filter membrane 34, the dialysate flows through a filter to remove the contaminants and then back to the Dialysate Reservoir where it is recirculated. The dialysis means shown in FIG. 3 is merely typical of such systems and it is not intended that this invention be limited to any particular dialysis apparatus or method, when incorporated as an optional additional feature. The embodiment of FIG. 3 may be used in conjunction with any of the embodiments previously disclosed, and in particular with the embodiments of FIGS. 1 and 2.

One important alternative offered by filtration technology as employed in this invention is the possibility of harvesting human leukocyte interferon (HuIFN) and other CPAS in a continuous or semi-continuous operation by diafiltration. It has been reported that high concentrations of HuIFN-α in a production broth may have an inhibitory effect on the leukocytes and therefore continual removal of HuIFN in accordance with the present invention may prolong the production time of HuIFN by the leukocytes. An additional advantage of the present invention, is that HuIFN is also purified and concentrated by utilizing filtration technology. The molecular cut-off characteristics of the membranes employed in such a step should be sized, so that water, salts, and low molecular weight species contaminants are eliminated, while retaining HuIFN on the perfusate (ex-filtrate) side of the cross-flow membrane.

Desalting and concentration by cross-flow filtration has been amply documented and it is believed to be a particularly advantageous process for biologically active molecules because of its inherent simplicity and absence of adverse effects, such as denaturation or shear-induced inactivation. These techniques are readily amenable to both pilot plant and full scale production of transfusable products, such as HSA and Factor VIII.

DISCUSSION OF EXAMPLES

Alpha-type human leukocyte interferon (HuIFN-α) was utilized in the examples of this invention as typical of CPAS generally and there is no reason to believe that the techniques disclosed in this invention for HuIFN-α extraction and purification cannot be utilized for any type of CPAS including interferon, lymphokines, monoclonal antibodies from hybridomas, etc. It is also believed that the fractional precipitation procedures currently utilized for extraction and purification are responsible for the presence of some contaminants. In fact, it is known that such processes inherently yield impure products, since the separation is based on the relative solubility of different molecular species in the same solvent.

Filtration technology, as used in the present invention, is better than fractional precipitation because it can remove from CPAS preparations high molecular weight species, which not only are the major contaminants, but are also possibly responsible for reported inflammatory and pyrogenic reactions. Moreover, filter technology is amenable to automation, does not require chemicals, and its efficiency can be readily improved since the only limiting factor is the surface area utilized for mass transfer. Finally, filtration has been shown to be a very gentle process with high discrimination capability, and obtainable yields of HuIFN are theoretically close to 100%.

EXAMPLES RELATED TO HuIFN-α PRODUCTION

Procurement of Human Leukocytes.

Plateletpheresis residues were obtained from the Washington Regional Red Cross Blood Services. The plateletpheresis procedures were performed according to standard procedures of the American Red Cross.

Upon receipt (less than six hours following collection) the plateletpheresis residues were characterized for white blood cell count using standard microscopic techniques. Red cells were lysed in a one-step procedure by addition to the residues of 0.83% ammonium chloride at room temperature at approximately a 1:5 volume to volume ratio. Incubation of the residues in ammonium chloride was conducted at room temperature for ten minutes. Subsequently, the preparation was centrifuged and the supernatant was discarded. This process was repeated a second time. The leukocytes obtained were then resuspended in incubation medium and subjected to white blood cell count to determine the extent of cell loss during the lysis procedure. Finally, the cells were transferred to incubation flasks and medium was added to achieve a concentration of about $1 \times 10^7$ cells/ml.

Incubation and Induction.

Medium for the short term culturing of normal human leukocytes obtained from residues of plateletpheresis procedures includes both the basic medium and additives. A typical medium for 5 liters was as follows:

| Chemical | Quantity |
| --- | --- |
| Eagle's Minimum Essential Medium (Powder, Grand Island Biological) | Powder for 5 liters |
| Tricine Buffer (Research Organics) | 15.0 grams |
| Human Serum Albumin (Cohn Fraction V) | 4.0 grams |
| MEM Nonessential Amino Acids (100 ×) (Grand Island) | 50.0 ml |
| MEM Sodium Pyruvate (100 ×) (Grand Island) | 50.0 ml |
| Sodium Bicarbonate | 6.0 grams |
| Gentamicin | 50.0 µg/l |
| Pyrogen-free water | 2 to 5 liters |

The medium was adjusted to a final pH of 7.4 and filtered under sterile conditions using positive nitrogen pressure, into suitable sterile containers.

All medium lots were tested for microbiological sterility as follows. To 20 tubes of thioglycollate broth were added 1.0 ml aliquots of each medium lot. Tubes were incubated for 21 days at 30°–32° C. and observed for growth. Fungal sterility was determined by testing 20–1.0 ml aliquots of medium in soybean-casein digest broth; incubation was for 21 days at 22°–25° C. Each lot was tested for viral contamination and ability to support growth of normal human cells by adding samples of EMEM test lots to subconfluent (80–85%) monolayers of human diploid fibroblasts (WI38). Cultures were held as long as possible and then subcultured with complete diploid growth medium containing 10% fetal bovine serum (which had been previously shown to be itself free of adventitious agents). Cultures were observed for cytopathology (CPE) and were subcultured to cover slips. Cover slips at confluency were fixed and stained with May Grünwald-Giemsa and observed for inclusions.

The CPAS inducer was Sendai virus (Cantell strain). The potency of each lot was measured by hemagglutination. The Sendai virus was added to the leukocyte preparations at a final concentration of 100–150 hemagglutinating units per ml of final mixture, thus affording a Production Broth.

Incubation was carried out in sterile wide-neck round bottom "boiling" flasks of 2-liter capacity. A magnetic stirrer of curved design, to spin on the curved flask surface, was aseptically added under a laminar flow hood. The incubation medium was first prewarmed to 37° C. Then purified leukocytes were added to give a final viable count of $1 \times 10^7$ cells per ml of mixture (by Trypan Blue Dye Exclusion), with final volumes of one half the capacity of each of the respective flasks. Priming interferon was then added to yield a final concentration of 100–200 international units per ml. After covering the mouths of the flasks with sterile aluminum foil, the flasks were submerged in water baths at 37° C. mounted over magnetic stirrers and the spinning bars were turned for two hours. The CPAS inducer (Sendai virus) was then added and incubation and stirring processes were continued from 16 to 18 hours.

In one example, the cells and debris were removed by low speed centrifugation at 1300 g for 45 minutes. The supernatant crude interferon was aseptically removed, tested for sterility, and stored at 4° C., before purification and concentration.

In another example, the supernatant was continuously removed. For this purpose, the incubation containers were connected through medical grade tubing to a 100,000 MW nominal cut-off hollow fiber filtration module. The suspension was pumped at different flow rates, and the filtrate collected and assayed for HuIFN-α activity. A pump was used to maintain a constant volume in the incubation flask by adding a volume of fresh MEM equal to the volume removed by filtration.

The method utilized to determine antiviral potency of the interferon preparations was the reduction of cytopathology of vesicular stomatitis virus (VSV)—infection on human foreskin cells.

Samples for assay were diluted in log steps in growth medium and 0.1 ml of each dilution were added to appropriate wells of Linbro ISFB$_{96}$ plates. From 5 to $8 \times 10^4$ trypsinized FS-7 cells were added to each well and plates were then incubated for 16 to 24 hours at 37° C. The VSV virus, prediluted to contain 6 to 10 plaque-forming units per cell, was added in 0.1 ml volume to wells containing diluted samples and the virus was also back-titrated in non-interferon containing wells. The plates were incubated for 48 hours or until cytopathic effect was complete. The cells were then fixed and stained with crystal violet-formalin washed and dried. The potency of each sample was determined by comparison to the standard HuIFN-α preparation treated identically.

Extraction and Purification of HuIFN-α.

The first series of experiments was designed to determine base line values for the efficiency of cross-flow filtration in accordance with this invention as a function of the operating parameters. In the extraction step, appropriate equipment with nominal molecular weight cutoff at 100,000 to 300,000 daltons was used in experiments where water, MEM, MEM+HSA and incubation medium, were perfused through a hollow fiber filtration module. The rate of filtration and the composition of the filtrate were determined as a function of perfusion time, transmembrane pressure, wall shear rate, and HSA concentration. The data obtained during this series was used to find the operational conditions necessary to obtain a high rate of filtration. A similar approach was taken for evaluation of the purification step, the only difference being the utilization of a filtration module with a lower nominal molecular cutoff (100,000 daltons) and that filtrate from the extraction step was used for perfusion, instead of MEM+HSA and incubation medium. The data indicated the operational requirements for filtration.

A second series of experiments was conducted differing in that partially purified HuIFN- was added to the perfusion media. HuIFN- was obtained for this purpose from the Finnish Red Cross in Helsinki. The transfer may have been somewhat hampered because of protein-protein or protein-membrane interaction. The HuIFN-α containing filtrate from the extraction step was utilized in the purification process.

The manner in which the HuIFN-α was extracted from the production broth is typical of CPAS extraction and is described with reference to FIG. 1. Production broth containing HuIFN-α was initially purified through a 100,000 dalton nominal molecular weight first cut-off filter at constant flow rate in a recirculation mode. HuIFN-α containing filtrate was diverted to a reservoir, from which it was pumped through a 10,000 dalton nominal molecular weight second cut-off filter at a constant flow rate in a recirculation mode. The filtrate from the second purification circuit was discarded as waste material. At the time of startup, the CPAS reservior/second filtration cell ciruit was activated as soon as enough fluid for priming was released from the first filtration cell. The CPAS reservoir/second filtration cell circuit acted to purify the extracted CPAS farther by removing smaller molecular particles in the filtrate. The second filtration cell filtrate was then discarded as per FIG. 1 or recycled to the production broth source as per FIG. 2. Further purification of the CPAS was optionally affected using dialysis apparatus as per FIG. 3.

EXAMPLE-SEPARATION ACCORDING TO FIG. 1

A separation was conducted using the apparatus and flow scheme of FIG. 1. HuIF-α was the CPAS, Sendai virus was the CPAS Inducer, and human leukocytes were the producing cells.

CELLS, MEDIA AND VIRUS

The source of leukocytes used for HuIFN-α production was plateletpheresis residues obtained from the Washington and the Chesapeake Regional Red Cross Blood Services. The residues were treated with 0.83% NH$_4$Cl, centrifuged, resuspended in NH$_4$Cl and recentrifuged. The leukocytes were then suspended in induction medium at a concentration of $5 \times 10^6$ to $1 \times 10^7$ cells/ml. Eagle's Minimum Essential medium was used, buffered with tricine and supplemented with human serum albumin (Cohn fraction V), non-essential amino acids, sodium pyruvate, sodium bicarbonate and gentamicin in glass distilled water. Leukocytes were "primed" with 250 international units of interferon per ml of reaction mixture. Two hours later, 150 HA units of Sendai virus "inducer" were added per ml of reaction mixture.

FILTRATION EQUIPMENT

All investigations were performed with Amicon flat sheet and hollow fiber membranes. The membranes were pre-treated with human serum albumin (HSA) by recirculating induction media. Transfer studies were conducted with a flat sheet membrane of 300,000 nominal molecular weight cut-off (MWC) and the following hollow fiber modules: H10×100 (9300 cm$^2$, 100,000 MWC, 1000 fibers with I.D.=0.5 mm), H1P100 (670 cm$^2$, 100,000 MWC, 250 fibers with I.D.=0.5 mm), Diafilter 20 (2000 cm$^2$, 50,000 MWC, 4000 fibers with I.D.=0.2 mm) and H1P10 (930 cm$^2$, 10,000 MWC, 870 fibers with I.D.=0.2 mm). The flat sheet membrane was tested in a straight channel differential filtration module with 6.25 cm$^2$ filtering area (channel height-×width=0.081×1.25 cm). Production and purification studies were conducted with H10X100, H1P100, H1P10 and Diafilter 20 hollow fiber modules.

ASSAY

Assays for interferon activity were perfomed by the Inhibition of Cytopathic Effect Method in 96 well microtiter plates. Serial two-fold dilutions of interferon samples were mixed with $1.5 \times 10^4$ to $2.0 \times 10^4$ Trisomic-21 or FS-7 human fibroblasts in grouwth medium and the cells were allowed to replicate overnight at 37° C. After removal of the interferon-medium mixture, 6 to 10 plaque-forming units per cell of vesicular stomatitis virus were added. Controls on each assay plate included cells in the absence of virus and cells with virus but without interferon. Serial dilutions of an internal interferon standard were used for calibration purposes. Plates were washed, fixed and stained with crystal violet dye, when virus controls indicated total cellular involvement, as manifested by cytopathic effect. The dye was eluted with ethylene glycol monomethyl ether and the amount of dye present determined by absorption measurements at 560 nm, using a multichannel photometer.

DATA ANALYSIS

Interferon titers were calculated using a computer program written specifically for this project. The input for each titer plate consists of absorbance values obtained from the multi-channel photometer, dilution factors and the nominal titer of the internal standard. The program calculates the percent dye uptake for each well as:

$$\% \text{ dye uptake} = \frac{A_{sample} - \bar{A}_{virus}}{\bar{A}_{cells} - \bar{A}_{virus}} \times 100 \tag{1}$$

where A = absorbance and $\bar{A}$ is the average of six absorbance values. The program selects dye uptake data in the range of 15 to 85% and performs linear regression for each sample. The 50% endpoints ($S_{50}$) are determined as:

$$S_{50} = \frac{50 - f}{k} \tag{2}$$

where $f$ = intercept and k = slope. The interferon titers are calculated relative to the internal standard as:

$$T_S = 2^{(S_{50} - IS_{50})} \times T_{IS} \times \frac{D_S}{D_{IS}} \tag{3}$$

where $T_S$ = sample titer, $IS_{50}$ = 50% endpoint of internal standard, $T_{IS}$ = internal standard titer, D = reciprocal of first dilution of sample and $D_{IS}$ = reciprocal of first dilution of internal standard. Values are ascertained for each sample relative to both internal standards and a mean value determined. A titer is also calculated for each internal standard sample relative to the other sample, assuming that the latter is the correct nominal titer. The program allows a tabulation of the interferon titers, the number of data points used for linear regression and the slopes, intercepts, correlation-coefficients and F-ratios obtained from linear regression for each sample.

Sieving coefficients (S) were determined as the ratio of interferon titer in the filtrate ($C_F$) over the titer in the perfusate ($C_p$):

$$S = (C_F / C_P) \tag{4}$$

Interferon production kinetics were analzed using an exponential model:

$$\log C(t) = e^{(\frac{a}{t^\alpha} + b)} \tag{5}$$

This mathematical model was chosen since it represents a sigmoidal function which assumes an asymptotic value when t becomes large:

$$\lim_{t \to \partial} C(t) = e^b = \text{constant}$$

A computer program was written in order to determine constants a, b, and $\alpha$ using regression analysis techniques.

The production rate was determined by the first derivative of C:

$$C'(t) = C(t) \ln 10 \frac{-a\alpha}{t^{\alpha+1}} e^{(\frac{a}{t^\alpha} + b)} \tag{7}$$

The time of maximum production rate was determined by solving the second derivative for t when $C'' = 0$ where:

$$C'' = ln10(C(t)y'' + C'(t)y') \tag{8}$$

where $$y' = \frac{-a\alpha}{t^{\alpha+1}} e^{(\frac{a}{t^\alpha} + b)} \tag{9}$$

and $$y'' = \left[ \frac{a^2\alpha^2}{t^{2(\alpha+1)}} + \frac{a\alpha(\alpha + 1)}{t^{\alpha+2}} \right] e^{(\frac{a}{t^\alpha} + b)} \tag{10}$$

EXPERIMENTAL PROCEDURES

Interferon transfer studies were conducted with the aforementioned membranes in a simple flow circuit. Media containing 2000 I.U./ml of purified HuIFN-α (obtained from the Finnish Red Cross Blood Transfusion Service) was recirculated through the filtration circuit and 2 ml samples were taken simultaneously from the perfusate and filtrate. The samples were stored at 4° C. and assayed for interferon activity the following day.

FIG. 1 shows the experimental arrangement to study interferon production, purification and concentration. Two identical 2 liter round-bottom flasks were used for interferon production. One flask was used for filtration studies while the other was used as a control. The suspension in the filtration vessel was recirculated through a 100,000 MWC hollow fiber where interferon solution was taken off as filtrate while cells and virus were retained. Cellular aggregates were retained in a pre-filter. The solution taken off as filtrate was replaced at an equal rate by fresh media that was pre-heated to 37° C. by pumping it through a plastic coil submerged in a waterbath. The interferon solution was fed to a reservoir from which it was recirculated through a 10,000 MWC or 50,000 MWC hollow fiber where excess media was taken off as filtrate while the interferon was retained. Samples were taken every 30 minutes from the filtration, control and reservoir vessels and immediately frozen in tubes submerged in a dry-ice ethanol mixture. The waste was collected in 8 liter flasks and a sample was taken from each flask. In addition, viable cell counts and pH measurements were done on samples from the filtration and control vessels once every hour. Inlet and outlet pressures were monitored throughout the experiment.

Filtration was discontinued when all the media (80–100 liters) had been used. Triplicate samples were taken from the filtration and control vessels and the vessels were left to incubate overnight. Final samples were taken in triplicate at 18 hours post induction.

| | INTERFERON TITERS (I.U./ML) | | |
|---|---|---|---|
| | REACTION FLASK | | TOTAL SYSTEM |
| | 4 hours | 18 hours | 18 hours |
| Conrol | 21,000 | 25,800 | 25,800 |
| Filtration | 3,800 | 21,000 | 25,300 |

EXPERIMENTAL CONCLUSIONS

The following parameters were investigated.
(1) Mass transfer of interferon across various ultrafiltration membranes;
(2) Rate of interferon production;
(3) Separation of interferon from an induction suspension containing leukocytes and virus and simultaneous concentration of the interferon solution.

A discussion of the above is as follows.

1. The mass transfer of interferon across various filtration membranes was studied. Both flat sheet membranes and hollow fibers, in the range of 10,000–3000,000 MWC (nominal molecular weight cut-off) were used. The transfer was 0% for 10,000 MWC, 5% for 50,000 MWC, 50% for 100,000 MWC and 100% for 300,000 MWC membranes. It should be noted that the membranes were pretreated with albumin and that the transfer probably involved an interferon-albumin complex.

2. The kinetics of interferon production in a batch system (Cantell procedure) were studied extensively in order to enable the design and analysis of the filtration process of this invention. A mathematical model was developed and a computer program written to aid in the analysis of experimental data. The results showed that the interferon production rate peaks at three hours post induction and decreases rapidly thereafter. This is in good agreement with the limited kinetic data available from Dr. Cantell's laboratory.

3. A laboratory-scale interferon production process based on filtration technology was designed and tested. The interferon-producing leukoycyte/virus suspension was recirculated through a 100,000 MWC cross-flow first filter and the interferon-containing filtrate was led to a reservoir from which the solution was recirculated through a 10,000 or 50,000 MWC filter. The filtrate from the second filter was either returned to the suspension or removed as waste, in which case fresh media was added to the suspension. Experiments proved that interferon was continuously removed from the induction suspension without adversely affecting the cells. The process was capable of producing the same amount of interferon per liter of suspension as a control batch (Cantell procedure). The interferon production kinetics are, however, different for the two systems. It is quite possible that the fitration process of this invention can be altered so as to take advantage of the different production kinetics in order to enhance the final yield of interferon, and still be within the disclosed inventive concept. As part of the experimental program, a cytopathic effect (CPE)-inhibition assay for interferon has been technically perfected. The method involves measurement of CPE-inhibition of serial dilutions of interferon on T-21 or FS-7 fibroblast cells using vesicular stomatitis virus (VSV) in 96-well microtiter plates. The CPE is determined indirectly through dye-uptake with absorption measurements using a multi-channel photometer. A computer program has been written in order to perform the extremely time-consuming calculations involved in an accurate analysis of the absorption data. The program provides a direct read-out of interferon titers and statistical data required for the evaluation of titer accuracy.

EXAMPLE-PERCENTAGE OF CPAS RECOVERY

Utilizing HuIFN-$\alpha$ as typical of CPAS, 100% recovery of purified CPAS was achieved, using the methods and apparatus of this invention. It is possible that some CPAS was lost during filtration because of adherence or binding of the CPAS molecules to the filtration membranes. It is also possible that continuous removal of the CPAS from the production broth permitted increased or continuing CPAS production by the cells. Since 100% of CPAS was recovered, as measured against an unfiltered control broth, the above phenomena either balance each other out, or may not be factors affecting separation efficiency.

EXAMPLE-SEMI-CONTINUOUS-FLOW METHOD

Utilizing HuIFN-$\alpha$ as the CPAS, enhanced recovery may be accomplished by continuous removal of the CPAS and subsequent cooling of the CPAS-containing filtrate. It is believed that a certain amount of HuIFN-$\alpha$ degradation may occur simultaneously with production at the optimum production temperature (37° C.), which degradation is reduced by lowering the CPAS-containing fluid temperature.

In an experiment which was not completed because of unrelated equipment failure, when filtrate from the second filtration cell was recycled to the production broth, the temperature was first raised to that of the production broth. The CPAS reservoir was maintained at the cooled temperature of 5° C. The apparatus used was that of FIG. 2. To achieve the desired heating and cooling, FIG. 2 was modified by adding a heating coil to the flow circuit between the second filtration cell 21 and the production broth, with a cooling coil being added between the first filtration cell 11 and the CPAS reservoir. The reason why CPAS degradation occurs at the optimum production broth temperature of 37° C. is not fully understood. It may be the result of CPAS thermal degradation or the result of the heat activation of other molecules which are present and which act upon the CPAS. In any case, it may be advantageous to reduce the temperature of the CPAS after it is separated from the production broth, while the production broth itself is maintained at its optimum production temperature. Maintenance of the optimum temperatures can be achieved by suitable insulation of the apparatus and/or the use of heating and/or cooling means, where appropriate.

What I claim is:

1. A separation method for extracting Cell-Produced-Antiviral-Substances (CPAS) from a production broth containing the living cells which produce the CPAS consisting essentially of:
subjecting said broth and said living cells to a non-dead-end membrane filtration wherein the broth and said living cells are perfused into a first filtration cell and caused to flow across an ultra-filtration membrane in said cell which membrane has a nominal molecular weight cut-off of from twice to about five times the maximum molecular weight of the CPAS,
permitting a first filtrate to pass through said membrane consisting essentially of CPAS and some molecular species,
retaining in a first retentate all remaining portions of said broth, and wherein a diafiltration process is afforded by a partially-closed cycle continuous or semicontinuous flow, in which said first filtrate removed from the broth is replaced with an equal volume of media, thus maintaining a constant suspension volume throughout the process, and said first retentate is cycled back to the broth.

2. The method of claim 1 wherein a dual module filtration process is afforded by perfusing the first filtrate containing the CPAS into a second filtration cell and causing it to flow across a second filtration membrane in said cell, which second membrane has a nominal molecular weight cut-off of about 75 percent or less of the minimum molecular weight of the CPAS and permits a second filtrate to pass through it, consisting essentially of all molecules smaller than the CPAS, which second filtrate is then discarded, the CPAS molecules being retained in the second retentate.

3. The method of claim 1 wherein a dual module diafiltration process is afforded by perfusing the first filtrae containing the CPAS into a second filtration cell and causing it to flow across a second filtration membrane in said cell, which second membrane permits a second filtrate to pass through it, consisting essentially of all molecules smaller than the CPAS, which second filtrate is then recycled to the broth together with the first filtrate, maintaining an approximately constant suspension volume in a partially-closed cycle continuous or semicontinuous flow process.

4. The method of claims 2 or 3 wherein from 1 to 3 additional filtration cells are incorporated within the cycle whereby the CPAS of the second retentate is further purified by the filtration removal of molecular species and other impurities, which molecular species and other impurities are recycled to the broth.

5. The method of claims 2 or 3 wherein the production broth contains genetically engineered animal cells capable of producing a CPAS or hybridomas capable of producing a monoclonal antibody CPAS.

6. The method of claim 5 wherein the CPAS is one of the group consisting of human interferons, non-human animal interferons, lymphokines, or monoclonal antibodies.

7. The method of claims 2 or 3 wherein the production broth contains a mixture of a naturally occurring animal cell suspension and a CPAS inducer.

8. The method of claim 7 wherein the CPAS is at least one the group consisting of human interferons, non-human animal interferons, and lymphokines.

9. The method of claim 8 wherein:
the cell suspension consists essentially of human leukocyte cells from plasma,
the CPAS inducer is a virus, and
the CPAS produced is alpha-type human interferon (HuIFN-$\alpha$) having a molecular weight range of about 15,000 daltons to about 21,000 daltons.

10. The method of claim 8 wherein:
the cell suspension consists essentially of human fibroblast cells,
the CPAS inducer is a virus, and
the CPAS produced is beta-type human interferon (HuIFN-$\beta$) having a molecular weight of about 24,000 daltons.

11. The method of claim 8 wherein:
the cell suspension consists essentially of human leukocyte cells from plasma,
the CPAS inducer is a mitogen, and
the CPAS produced is gamma-type human interferon (HuIFN/$\gamma$) having a molecular weight range of about 40,000 daltons to about 75,000 daltons.

12. A dual module separation apparatus for extracting purified Cell-Produced-Antiviral-Substances (CPAS) from a CPAS production broth containing living cells which produce said CPAS consisting essentially of:
a source of production broth containing said living cells;
first non-dead-end filtration cell means, conduit means flowingly connecting said source of production broth containing said living cells to said first non-dead-end filtration cells means for flowing said broth and living cells across a filtration membrane for separating CPAS and all smaller molecules in a filtrate and recycling a retentate back to said source of production broth containing said living cells, which membrane has a nominal molecular weight cut-off of from twice to about five times the maximum molecular weight of said CPAS;
CPAS reservoir means for receiving and storing said CPAS;
conduit means flowingly connecting said first non-dead-end filtration cell means to said CPAS reservoir means for conducting said filtrate to said CPAS reservoir means;
second filtration cell means for separating molecules smaller than CPAS into a second filtrate and a second retentate containing CPAS, said second filtration cell means having a filtration membrane with a nominal molecular weight cut-off of about 75 percent or less of the minimum molecular weight of the CPAS;
and
conduit means flowingly connecting said second filtration cell means with said CPAS reservoir for conducting fluid from said CPAS reservoir to said second filtration cell means and for recycling said second retentate back to the CPAS reservoir.

13. The apparatus of claim 12 further comprising:
a production broth reservoir containing a CPAS;
a first non-dead-end conduit leading from said production broth reservoir to a first filtration cell;
said first filtration cell having a retentate chamber receiving the production broth from the first conduit, a second conduit leading from the retentate chamber back to the production broth reservoir, a filtrate chamber separated from the retentate chamber by a filtration membrane so that a perfusate into the cell flows across said membrane, which is sized to permit the passage of CPAS and all smaller or equal sized molecules;

a third conduit leading from said filtrate chamber to a CPAS reservoir;

a fourth conduit leading from said CPAS reservoir to a second filtration cell;

said second filtration cell having a second retentate chamber receiving the contents of the CPAS reservoir from the fourth conduit, a fifth conduit leading from the second retentate chamber back to the CPAS reservoir, a second filtrate chamber separated from the second retentate chamber by a second filtration membrane sized to permit the passage of all molecules smaller than the CPAS;

a sixth conduit leading from the second filtrate chamber to a waste disposal means:

means for adding production broth replacement ingredients to the production broth reservoir at a rate equal to that of the CPAS and smaller molecules removal; and pumping means for maintaining flow through the conduits and throughout the apparatus at about a constant pressure or flow rate.

14. The apparatus of claim 12 or 13 wherein the filtrate from the second filtration cell is recycled by a seventh conduit, back to the production broth source.

15. The apparatus of claim 14 wherein a diafiltration circuit is included in a conduit between the CPAS reservoir and the second filtration cell.

16. The apparatus of claim 14 wherein cooling means are located between the first filtration cell and the CPAS reservoir, and heating means are located between the second filtration cell and the production broth source.

17. The apparatus of claim 12 or 13 wherein a dialysis circuit is included in a conduit between the CPAS reservoir and the second filtration cell, to remove contaminant salts.

18. The apparatus of claim 12 or 13 wherein the CPAS production broth consists essentially of CPAS producing cells CPAS inducer, culture media and culture adjuvants.

19. The apparatus of claim 12 or 13 wherein the CPAS producing cells consist essentially of human leucocytes, the CPAS inducer is a virus, and the CPAS is alpha-type human interferon.

20. The apparatus of claim 12 or 13 wherein the CPAS producing cells consist essentially of human fibroblast cells, the CPAS inducer is a virus, and the CPAS is beta-type human interferon.

21. The apparatus of claim 12 or 13 wherein the CPAS producing cells consist essentially of human leucocyte cells from plasma, the CPAS inducer is a mitogen, and the CPAS in gamma-type human interferon.

22. The apparatus of claim 12 or 13 wherein the CPAS is a lymphokine or monoclonal anitbody.

23. The apparatus of claim 12 or 13 wherein the CPAS producing cells consist essentially of genetically-engineered bacteria or hybridomas.

24. The apparatus of claim 12 or 13 wherein cooling means are located between the first filtration cell and the CPAS reservoir.

* * * * *